US011413251B2

(12) United States Patent
Dick et al.

(10) Patent No.: US 11,413,251 B2
(45) Date of Patent: *Aug. 16, 2022

(54) GELATIN PRODUCT COMPRISING A CORE COMPONENT AND METHOD FOR PRODUCING SAME

(71) Applicants: GELITA AG, Eberbach (DE); WINKLER UND DÜNNEBIER SÜSSWARENMASCHINEN GMBH, Rengsdorf (DE)

(72) Inventors: Eberhard Dick, Neckargemünd (DE); Sarah Engelhardt, Rothenberg (DE); Johanna Schmidgall, Heilbronn (DE); Holger Brack, Rümmelsheim (DE); Andre Weins, Neuwied (DE)

(73) Assignees: GELITA AG, Eberbach (DE); WINKLER UND DÜNNEBIER SÜSSWARENMASCHINEN GMBH, Rengsdorf (DE)

( * ) Notice: Subject to any disclaimer, the term of this patent is extended or adjusted under 35 U.S.C. 154(b) by 162 days.

This patent is subject to a terminal disclaimer.

(21) Appl. No.: 16/598,826

(22) Filed: Oct. 10, 2019

(65) Prior Publication Data

US 2020/0038335 A1 Feb. 6, 2020

Related U.S. Application Data

(63) Continuation of application No. PCT/EP2018/056877, filed on Mar. 19, 2018.

(30) Foreign Application Priority Data

Apr. 11, 2017 (DE) .......................... 102017107845.2

(51) Int. Cl.
| | |
|---|---|
| A61K 9/16 | (2006.01) |
| A61K 9/50 | (2006.01) |
| A23P 30/10 | (2016.01) |
| A23L 29/281 | (2016.01) |
| A23G 3/44 | (2006.01) |
| A61K 9/00 | (2006.01) |

(52) U.S. Cl.
CPC .............. *A61K 9/5057* (2013.01); *A23G 3/44* (2013.01); *A23L 29/284* (2016.08); *A23P 30/10* (2016.08); *A61K 9/0056* (2013.01); *A61K 9/5015* (2013.01); *A61K 9/5089* (2013.01); *A23V 2002/00* (2013.01)

(58) Field of Classification Search
CPC ........ A61K 9/056; A61K 9/053; A61K 9/058; A61K 9/006; A61K 9/20; A61K 9/2004; A61K 9/2013; A61K 9/2018; A61K 9/2054; A61K 9/2059; A61K 9/2072; A61K 9/2095; A61K 9/205; A61K 9/0056
See application file for complete search history.

(56) References Cited

U.S. PATENT DOCUMENTS

| | | | | |
|---|---|---|---|---|
| 2004/0013732 | A1* | 1/2004 | Farber | A23G 3/346 424/488 |
| 2007/0148292 | A1 | 6/2007 | Royo et al. | |
| 2010/0119663 | A1 | 5/2010 | Marshall et al. | |
| 2013/0337096 | A1* | 12/2013 | Purcell | A61K 38/17 424/773 |
| 2014/0127375 | A1* | 5/2014 | Cao | A23G 3/44 426/576 |
| 2017/0086475 | A1 | 3/2017 | Dick et al. | |
| 2018/0289032 | A1* | 10/2018 | Dick | A61P 3/02 |

FOREIGN PATENT DOCUMENTS

| | | |
|---|---|---|
| DE | 60223269 T2 | 8/2008 |
| EP | 1429738 B1 | 10/2007 |
| EP | 2762006 A1 | 8/2014 |
| JP | 08009901 A * | 1/1996 |
| JP | H8-9901 A | 1/1996 |
| JP | H089901 A | 1/1996 |
| JP | 2011-234654 A | 11/2011 |
| WO | WO 2005/094782 A1 | 10/2005 |
| WO | WO 2011/054049 A1 | 5/2011 |
| WO | WO 2013/163240 A1 | 10/2013 |
| WO | WO 2015/193300 A1 | 12/2015 |

OTHER PUBLICATIONS

Badii et al (Fish Gelatin: Structure, gelling properties and interaction with egg albumin proteins, Food Hydrocolloids, 20, 2006, 630-640) (Year: 2006).*
International Bureau, International Search Report and Written Opinion in International Application No. PCT/EP2018/056877, dated May 17, 2018.
Wasswa et al., "Utilization of Fish Processing By-Products in the Gelatin Industry," *Food Reviews International*, 23(2): 159-174 (2007).

* cited by examiner

*Primary Examiner* — Micah Paul Young
(74) *Attorney, Agent, or Firm* — Leydig, Voit & Mayer

(57) ABSTRACT

The present invention relates to a gelatin product comprising a core component, wherein the core component is encased partially or fully by a gelatin gel. The gelatin gel is produced from a homogeneous casting compound containing the following constituents dissolved in water:
- 3 to 20 wt % of gelatin having a mean molecular weight, determined by gel chromatography, of at least 130 kDa, wherein the proportion of the molecular weight fraction above 100 kDa is at least 35 wt %;
- up to 60 wt % of glucose syrup with a viscosity of less than 1000 mPa·s, measured with a dry matter content of 80 wt % and at a temperature of 60° C.; and
- up to 60 wt % of sucrose, wherein the casting compound comprises a dry matter content of at least 70 wt %.

20 Claims, No Drawings

GELATIN PRODUCT COMPRISING A CORE COMPONENT AND METHOD FOR PRODUCING SAME

CROSS-REFERENCE TO RELATED APPLICATIONS

This patent application is a continuation of International Patent Application No. PCT/EP2018/056877, filed on Mar. 19, 2018, which claims the benefit of German Patent Application No. 10 2017 107 845.2, filed on Apr. 11, 2017, which are incorporated herein by reference.

THE NAMES OF THE PARTIES TO A JOINT RESEARCH AGREEMENT

The presently claimed invention was made by, or on behalf of, the below listed parties to a joint research agreement. The joint research agreement was in effect on or before the effective filing date of the present application. The claimed invention was made as a result of activities undertaken within the scope of the joint research agreement. The parties to the joint research agreement are Gelita AG and Winkler and Dünnebier Süsswarenmaschinen GmbH.

FIELD OF THE INVENTION

The present invention relates to a gelatin product comprising a core component, wherein the core component is encased partially or fully by a gelatin gel.

The invention also relates to a method for producing gelatin products of this type.

The generic term "gelatin products" as used hereinafter includes on the one hand popular sugar confectionery products characterised primarily by a more or less elastic texture of the gelatin gel. Besides the gelatin, various sugar types and/or sugar substitutes form the main constituent of these products, which can be referred to in the broadest sense as gummy sweets, and in particular are known in the form of gummy bears or fruit gums.

On the other hand, such gelatin products are also used as chewable tablets in the field of dietary supplements and medicinal products, wherein various nutrients (for example vitamins, minerals or peptides) and/or pharmaceutical active substances are added to the basic recipe. The sugar content can be reduced in this case, wherein the transition from confectionery to dietary supplements is rather blurred. Gummy sweets or chewable tablets enriched with various additives or active substances are offered for example as what are known as "fortified gummies".

In the case of the generic gelatin products comprising a core component, additives of this kind are contained in the core component instead of in the outer gelatin gel. This has various advantages. For example, pharmaceutical active substances that have insufficient temperature stability could not be easily added to the gelatin gel, since the casting compound used for production has to be heated to at least 75° C. An addition of water-insoluble active substances or nutrients to the gelatin gel is also unfavourable, since it is difficult to produce a homogeneous distribution and reproducible dosing in the case of a suspension in the casting compound, and because insoluble substances of this kind lead to a clouding of the gelatin gel. Lastly, the colour and taste of active substances or nutrients of this kind can have a very negative effect on the palatability, or might not even be possible on account of unfavourable chemical or physical properties (such as high pH values, susceptibility to hydrolysis, etc.) of the produced product.

A core component, which for example can be based on a solid-substance mixture, thus constitutes an advantageous possibility for administering a wide range of active substances and/or nutrients in the form of gelatin products, in particular because the thermal loading of the active substances is much lower. The high overdosages, which are otherwise standard, are therefore generally no longer necessary, or it becomes possible to add certain active substances, which leads to a much more economical use of the active substance components, which are often costly, or enables new products to be created.

The previously used production method for gelatin products is known as the mogul technique. In this method, a hot casting compound having a water content of approximately 25 wt % and containing the gelatin, the sugar and the other constituents dissolved in water is poured into hollow moulds formed from a starch moulding powder. The hollow moulds are produced beforehand by pressing a positive mould into the smooth surface of a flat tray filled with dry starch powder. Once the hollow moulds have been filled, the starch powder trays are stored for between 24 and 72 hours in a climatic chamber. During this time, the casting compound in the hollow moulds cools, which causes the cast article to set. In parallel hereto, some of the water is absorbed by the starch moulding powder, such that a drying process takes place, wherein the finished gelatin products generally have a water content of approximately 20 wt % or less, so as to attain an $a_w$ value that ensures the microbiological stability. The powder trays are then emptied, and the starch moulding powder is separated from the gelatin products by means of sieving and is re-used after having been dried. The gelatin products are treated with a release agent or with crystallised sugar ("lubrication" or sugar coating) in order to prevent any sticking, and are packaged.

The use of starch moulding powder for the production of the hollow moulds is associated with various disadvantages. Due to the long drying time (24 to 72 hours) of the gelatin products cast in starch moulding powder using the known recipes, large drying chambers and a very high number of moulding powder trays are required in the case of suitably high-performance mogul plants, which cast up to 35 powder trays per minute. The space requirement and the necessary investment for climate control, moulding powder trays, starch dryers, and not least the starch moulding powder are therefore considerable. The contamination of the production areas with starch powder, which cannot be completely avoided in spite of constant cleaning, is also problematic.

A further disadvantage of the mogul method is the risk of cross-contamination in the event of a product change, since contaminations of the previously produced product always remain in the starch and can be introduced into the new product with continuous re-use of the starch moulding powder. This problem could be avoided only by discarding all of the starch moulding powder prior to each product change, however this would be completely uneconomical.

The described disadvantages of the known production method are extremely critical in particular for the production of pharmaceutical products. With regard to hygiene (contamination by starch dust) and purity (cross-contamination), the mogul technique does not meet the demands of the pharmaceutical standards (GMP guidelines) and thus severely restricts the fields of application of gummy sweets or chewable tablets as medicinal dosage forms. This is true with limitations (for example thermal load) also for gelatin products comprising a core component, more specifically regardless of whether an active substance is contained in the gelatin gel and/or in the core component. Since the core component has to be introduced into the gelatin products within the scope of the casting process, additional problems can also occur during the course of the process on account of the fundamental instability of the starch moulds.

The use of solid, re-usable hollow moulds (in particular made of plastics material) for the casting of gelatin products of this type previously failed for economical and technical reasons. Such methods are indeed known for the production of sugar confectionery products based on other, rapidly setting hydrocolloids (such as pectin), which allow a low viscosity of the casting compound. However, the sensory properties of these products differ significantly, and therefore they are not considered by consumers to constitute an alternative to gelatin products.

It is not possible to dry the known gelatin-based casting compounds in solid hollow moulds, since in that case water would be able to escape only via the open upper side. This is not sufficient for complete and homogeneous drying. A subsequent drying after the demoulding is likewise problematic and difficult to implement, since the surface of the products dries more quickly compared to the core and a diffusion of the water from the inside out is inhibited (skin formation).

Changes to the recipe are very difficult, since different, sometimes contrary basic conditions must be observed: On the one hand, the rheological properties of the casting compound must be suitable for the casting process, and on the other hand, the end product should have the typical texture of gelatin products expected by the consumer.

BRIEF SUMMARY OF THE INVENTION

The object of the present invention is therefore to propose a gelatin product comprising a core component, which product can be produced using a method suitable for pharmaceutical products, in particular by casting of the gelatin gel in solid hollow moulds.

This object is achieved in accordance with the invention in the case of the gelatin product of the type mentioned in the introduction in that the gelatin gel is produced from a homogeneous casting compound containing the following constituents dissolved in water:
  3 to 20 wt % of gelatin having a mean molecular weight, determined by gel chromatography, of at least 130 kDa, preferably at least 145 kDa, wherein the proportion of the molecular weight fraction above 100 kDa is at least 35 wt %, preferably at least 45 wt %;
  up to 60 wt %, preferably 15 to 60 wt %, of glucose syrup with a viscosity of less than 1000 mPa·s, preferably less than 800 mPa·s, measured with a dry matter content of 80 wt % and at a temperature of 60° C.; and
  up to 60 wt %, preferably 15 to 60 wt %, of sucrose, wherein the casting compound comprises a dry matter content of at least 70 wt %.

DETAILED DESCRIPTION OF THE INVENTION

It has surprisingly been found that, during the cooling after the pouring, a casting compound having this composition is able to achieve the texture and consistency typical for gelatin products merely by the setting of the gelatin, without the need for significant drying, i.e. a release of water, for this purpose. This is made possible in that the casting compound substantially already has the same low water content as the gelatin gel to be produced of the gelatin product according to the invention.

In spite of the higher dry matter content compared to the prior art, the casting compound has, on account of its components, rheological properties which allow processing in the conventional way. On the one hand, a sufficiently low viscosity of the hot casting compound and, on the other hand, a rapid solidification of the system during cooling are decisive factors. Only in this way can undesirable phenomena such as filament formation and/or air inclusions be avoided alongside good demouldability.

Due to these properties, the casting compound can be cast, in the case of production of gelatin products according to the invention, in solid hollow moulds in particular made of a plastics material, such as silicone, polycarbonate or PET. Besides the advantages resulting here from the omission of the previously used starch moulding powder, this also leads to a significant shortening of the production method, since the casting compound is generally solid enough in less than just 60 minutes to be able to be demoulded without excessive adhesion. By contrast, the products cast using the known recipes in starch moulding powder require between 24 and 72 hours to dry. The speed-determining step for the demoulding is in this case the drying, and not the gel formation. An acceleration of the gel formation would even lead to a significant slowing of the drying and therefore would not be expedient.

The invention thus leads, with a comparable productivity per unit of time, to a significantly reduced space requirement for the cooling gelatin products, which significantly lowers the investment for the hollow moulds and the storage space for the drying, which is no longer required, and also the operating costs (no starch drying or climate control of the storage areas).

The casting compound used for the gelatin products according to the invention achieves the stated object by means of the cooperation of the contained components within the above-mentioned quantity ranges. An essential feature of the invention is the selection of a high-molecular gelatin with a mean molecular weight, determined by gel chromatography, of at least 130 kDa, wherein the proportion of the molecular weight fraction above 100 kDa is at least 35 wt %. Such gelatins can be obtained from various collagen-containing materials, in particular from connective tissue or bones of pigs, cattle, poultry or fish.

Flavourings, colourings and/or acidifiers can be contained as further components in the casting compound, wherein the typical quantity proportions of such additives are known from the prior art. The conventional edible acids, preferably citric acid, are used as acidifier.

The gelatin is contained in the casting compound in a proportion of from 3 to 20 wt %, wherein a proportion of from 5 to 12 wt % is preferred, in particular from 6 to 10 wt %. Within this range, gelatin products that have a typical texture, in particular a high elasticity, are obtained.

Glucose syrup and sucrose can be contained in the casting compound in a proportion of, in each case, up to 60 wt %, preferably (apart from in the case of sugar-free gelatin products) in each case from 15 to 60 wt %. The casting compound more preferably contains in each case 20 to 40 wt % of glucose syrup and/or sucrose. However, these components can also be omitted for the production of sugar-free products and can be replaced by a corresponding proportion of sugar substitutes, in particular sugar alcohols.

With use of glucose syrup, this has a viscosity of less than 1000 mPa·s, preferably of less than 800 mPa·s, measured with a dry matter content of 80 wt % and at a temperature of 60° C. The glucose syrup is conveniently a highly hydrolysed glucose syrup with a dextrose equivalent of 50 or more, preferably of 60 or more.

In a further embodiment of the invention the casting compound also contains one or more sugar substitutes, in particular sugar alcohols, in a proportion of up to 80 wt %, preferably from 10 to 50 wt %. Due to the use of sugar substitutes, the quantity of sucrose and/or glucose syrup can be reduced on the one hand (down to zero in the case of sugar-free products), and on the other hand the sugar alcohols also contribute to the favourable rheological properties of the casting compound The one or more sugar alcohols is/are preferably selected from sorbitol, mannitol, xylitol, erythritol and glycerol. When other sugar substitutes are used, these are preferably selected from polydextrose, hydrogenated glucose syrup (for example Lycasin) and resistant dextrin (for example Nutriose).

In accordance with a variant of the invention, the casting compound also comprises one or more further hydrocolloids, in particular pectin, agar, carrageenan or starch, in order to modify the properties of the gelatin products (for example temperature stability and elasticity). The proportion of further hydrocolloids is preferably from 0.1 to 10 wt %, in particular from 0.2 to 5 wt %.

The gelatin gel produced from the casting compound encases a core component in the produced gelatin product, the composition and properties of said core component being discussed hereinafter. The core component is preferably fully encased by the gelatin gel, but a partial encasement is also possible within the scope of the invention.

In principle, the composition and appearance of the core component can vary across a wide range, and any ingredients that are suitable in principle for use in sugar confectionery products or pharmaceutical products can be used for the production of the core component. The core component can be solid, gel-like or liquid.

In a preferred embodiment of the invention the core component is a shaped body that is produced from a solid-substance mixture, in particular by compression, compaction, tableting or granulation. A core component of this kind is advantageous in particular for a pharmaceutical application of the gelatin product according to the invention. In this regard the core component can have in particular the appearance of a pharmaceutical tablet, but with smaller dimensions compared to conventional tablets as appropriate.

Alternatively, "conventional" sugar confectionary products can also be used as core component, such as hard caramels or chocolate, or also nuts and fruits (or parts thereof).

In a particular embodiment of the invention the shaped body has a characteristic shape, surface structure and/or colour, so as to enable the gelatin product to be visually recognisable. A characteristic shape is intended to mean, in particular, that the shaped body deviates significantly from a simple geometric shape, such as a sphere, an ellipsoid, or a cylinder. The characteristic surface structure can be in particular the impression of a pattern or the like.

Since the surrounding gelatin gel is typically transparent, the overall product can be provided very easily with a typical appearance by the characteristics of the core component. This is independent of the external shape of the gelatin product. For example, product-specific or brand-specific markings can thus be produced very easily and economically, without having to change the hollow moulds, which determine the external shape of the gelatin product.

The core component favourably comprises one or more sugars, sugar substitutes and/or polysaccharides as basic constituents, wherein these basic constituents preferably form the majority of the core component, i.e. a proportion of more than 50 wt %, more preferably of more than 70 wt %. The basic constituents of the core component can be selected in particular from glucose, fructose, lactose, sucrose, sorbitol, mannitol, xylitol, erythritol, starch, modified starch, cellulose, modified cellulose, and mixtures thereof. If necessary, the core component can also comprise a small proportion of additives for the tableting, these being known from the prior art (for example flow aids, anti-adhesive agents)

As already mentioned above, it is particularly advantageous within the scope of the invention when the core component comprises one or more pharmaceutical active substances and/or nutrients. The gelatin products according to the invention can thus be used for example in the form of chewable tablets, as a pharmaceutical dosage form, or as a dietary supplement. Preferred nutrients in the core component are selected from vitamins, minerals, plant extracts and peptides, in particular collagen peptides (collagen hydrolysate).

In the field of the pharmaceutical application, all active substances that are also otherwise suitable for solid dosage forms can be used in principle in the core component of the gelatin product according to the invention. Here, painkillers such as acetylsalicylic acid, paracetamol, or ibuprofen are cited, merely by way of example. The dosing thereof, however, is relatively high in contrast to the known solid dosage forms, i.e. the core component in this case preferably comprises a small proportion of the above-mentioned basic constituents and the pure pharmaceutical active substance.

A pharmaceutical active substance can be added particularly advantageously to a mixture of the basic constituents, in particular a solid-substance mixture, and can be compressed, compacted, tableted or granulated into a shaped body to produce the core component, as has already been discussed further above. In contrast to an addition to the casting compound from which the gelatin gel is formed, the pharmaceutical active substance is not exposed here to any thermal loading. Since the gelatin products according to the invention can be cast in solid hollow moulds by the use of the above-described casting compound, it is possible to ensure that the hygiene standards applicable in the pharmaceutical field (GMP guidelines) are observed, in contrast to the mogul technique.

A further significant advantage in respect of the production of the gelatin product according to the invention can be achieved in that the core component has hygroscopic properties. This means that the core component, once it has been encased by the casting compound during the production process, removes water therefrom depending on the difference between the water contents of the casting compound and core component and depending on their hygroscopicities. The resultant balancing of the concentration gradient by diffusion of water in accordance with Fick's law of diffusion leads to a total water content of the gelatin product which, with appropriate selection of the water contents of the gelatin gel and of the core component, gives an $a_w$ value with sufficient microbiological stability. Here, the core component can be softened or liquefied as appropriate. Suitable hygroscopic constituents of the core component are in particular sugar and sugar substitutes.

The finished gelatin product in accordance with the invention preferably has a dry matter content of more than 80 wt % and/or a water activity ($a_w$ value) of less than 0.75, preferably less than 0.7. As already mentioned, a somewhat higher water content of the casting compound can also be compensated here by a core component having an accordingly low water content.

The core component typically accounts for a proportion of from 2 to 60% of the total mass of the gelatin product, preferably from 5 to 40%, in particular from 10 to 30%. The lower limit is given substantially from the manageability and required mass to introduce the desired quantity of a pharmaceutical active substance or nutrient into the gelatin product. The upper limit is given substantially on the basis of the fact that the proportion of the gelatin gel must be sufficient to ensure complete encasement of the core component.

The gelatin product according to the invention can typically have a total mass in the range of from 1 to 10 g, wherein the mass of the core component lies accordingly preferably in the range of from 0.02 to 6 g.

As already mentioned in the introduction, the term "gelatin products" within the scope of the present invention includes all sweet confectionery products, dietary supplements or medicinal products having the corresponding composition, regardless of their external shape. Typical examples of such products are gummy sweets, fruit gums, fortified gummies, chewable tablets, etc.

The gelatin products according to the invention preferably have a dry matter content of at least 80 wt % and/or a water activity ($a_w$ value) of less than 0.75. As already described in conjunction with the casting compound, there is no, or only an insignificant increase of the dry matter content during the cooling and setting.

The present invention also relates to a method for producing the gelatin product comprising a core component according to the invention, said method comprising the following steps:
  pouring a first amount of the casting compound at a temperature of 75° C. or more into a hollow mould;
  cooling the casting compound as appropriate, in particular to a temperature of from 30 to 50° C.;
  placing the core component in the hollow mould;
  pouring a second amount of the casting compound at a temperature of 75° C. or more into the hollow mould;
  cooling the casting compound in the hollow mould to a temperature of 25° C. or below in order to obtain the gelatin product; and
  removing the gelatin product from the hollow mould as appropriate.

On account of the advantages of the used casting compound already described above, the method according to the invention is suitable in particular for casting in solid hollow moulds. Nevertheless, the method according to the invention can also be performed with hollow moulds in a starch moulding powder in accordance with the known mogul technique.

In principle any material, in particular plastics material, which is temperature stable (up to approximately 95° C.) and which is suitable for contact with foodstuffs can be used for the production of solid hollow moulds. Hollow moulds made of silicone, which on account of its flexibility enables easy demoulding of the gelatin products, are particularly preferred.

Further examples of suitable plastics materials are polycarbonate (PC) or polyethylene terephthalate (PET), for example, and also composite materials in which different properties (oxygen barrier, anti-adhesion, etc.) are combined. Hollow moulds can be produced from thin films of these plastics by means of thermoforming, similarly to the known blister packs for medicinal drugs. These materials are more economical than silicone, which opens up the possibility of producing individualised hollow moulds, for example having inscriptions which are impressed into the gelatin products. These hollow moulds can then be discarded after relatively few production cycles. By contrast, silicone is indeed more costly, but can be used for much longer and much more frequently.

The casting compound is cooled in the hollow mould preferably within a period of less than 60 min, more preferably less than 45 min. This relatively short period of time, after which the gelatin product can already be removed from the hollow mould, constitutes a significant advantage over the mogul technique and the casting compounds used there, where the gelatin products usually can be removed only after a drying time of from 24 to 72 hours.

The casting compound is preferably cooled in the hollow mould by means of an active cooling of the hollow mould, which likewise is not possible in the case of the mogul technique.

Once the gelatin products have been removed from the hollow moulds, they can be either treated with a release wax or dusted with sucrose and/or citric acid, depending on the desired look.

In accordance with a further embodiment of the invention the gelatin product is not removed from the hollow mould after the cooling of the casting compound, and instead remains in the hollow mould until consumed by the consumer. In this case the hollow mould is typically formed as part of a blister pack and is made for example of PC, PET or a composite material. Gelatin products according to the invention can be produced in a blister pack of this kind and can be sold as a pharmaceutical dosage form.

These and further advantages of the invention will be explained in greater detail on the basis of the following examples.

EXAMPLES

Gelatin products according to the invention were produced in accordance with the method described hereinafter from two different casting compounds and six different core components (Examples 1 to 6).

Production of the Gelatin Products

For this purpose, the gelatin was firstly dissolved completely in hot water (70 to 80° C.), then sorbitol and glycerol were added as appropriate, and the mixture was stirred homogeneously and was heated again to 70 to 80° C.

In parallel, a so-called sugar slurry was produced by boiling glucose syrup, sucrose, and as appropriate pectin in water under pressure to at least 110° C. The gelatin solution prepared previously was added (as appropriate with addition of sorbitol and glycerol) either before or after the heating of the sugar slurry. In the case of the subsequent addition, the sugar slurry was cooled to approximately 100° C. and the gelatin/sorbitol solution were combined. This mixture was degassed under vacuum and cooled to the casting temperature. During the degassing, the water content of the composition was also reduced to such an extent that the dry matter content was at least 70 wt %.

Citric acid was then added as acidifier, as well as colourings and flavourings, and the casting compound was filled into hollow moulds made of silicone (Examples 1 to 5) or into hollow moulds in a PET blister pack (Example 6) in two steps. For this purpose, a pilot installation for starch-free casting from the company WINKLER und DÜNNEBIER Süßwarenmaschinen GmbH, Rengsdorf, was used. The centred placement of the core component (see below) between the two pouring steps was performed likewise by means of a special installation component from the company WINKLER und DÜNNEBIER ("Pick and Place" inserter).

The filling quantity of the casting compound was in each case between 3 and 5 g. After a cooling time of at most 60 min at less than 12° C. ambient temperature, the gelatin products according to the invention (gummy sweets/chewable tablets) could be demoulded. The products can then be lubricated as desired using a release wax or dusted with sugar and citric acid and then packaged.

The core components were produced from a solid-substance mixture (powder mix) having the composition specified in each case, with the aid of a commercially available tablet press. In so doing, different variants in respect of the shape and weight were also realised. Of course, other shaping methods are also suitable for the powder mixes described hereinafter.

Composition of the Casting Compound

The compositions of the casting compound for the respective examples are specified in the following table. The gelatin solution was added (as appropriate with addition of sorbitol and glycerol) before the heating of the sugar slurry.

| Components in wt % | Examples 1 to 3 | Examples 4 to 6 |
|---|---|---|
| Sugar slurry: | | |
| Sucrose | 20.3 | 35.5 |
| Glucose syrup DE 60 | 38.2 | 35.5 |
| Sorbitol | 13.3 | — |
| Glycerol | 3.3 | — |
| Water | 5.4 | 9.5 |
| Gelatin solution: | | |
| Gelatin | 5.5 | 5.5 |
| Water | 11.0 | 11.0 |
| Citric acid (50%) | 2.0 | 2.0 |
| Colourings | 0.5 | 0.5 |
| Flavourings | 0.5 | 0.5 |

Composition of the Core Component

The composition, the shape, and the weight of the core component are specified hereinafter for the respective examples.

Example 1

| Dextrose | 92.5 wt % |
|---|---|
| Magnesium stearate | 0.5 wt % |
| Citric acid | 5.0 wt % |
| Colourings and Flavourings | 2.0 wt % |
| Shape | cylindrical, flat |
| Weight | 1.0 g |
| Dry matter content | 98.2 wt % |

Example 2

| Sorbitol | 37.8 wt % |
|---|---|
| Caffeine/Taurine 1:1 | 60.0 wt % |
| Magnesium stearate | 0.2 wt % |
| Colourings and Flavourings | 2.0 wt % |
| Shape | star-shaped, flat |
| Weight | 0.615 g |
| Dry matter content | 97.5 wt % |

Example 3

| Sorbitol | 37.8 wt % |
|---|---|
| Vitamin/Mineral mix | 60.0 wt % |
| Magnesium stearate | 0.2 wt % |
| Colourings and Flavourings | 2.0 wt % |
| Shape | Letter W |
| Weight | 0.5 g |
| Dry matter content | 98.2 wt % |

Example 4

| Dry glucose syrup | 20.5 wt % |
|---|---|
| Sodium ascorbate/Ascorbic acid 3:2 | 75.0 wt % |
| Magnesium stearate | 0.5 wt % |
| Highly disperse $SiO_2$ | 0.1 wt % |
| Colourings and Flavourings | 2.0 wt % |
| Shape | Letter C |
| Weight | 0.8 g |
| Dry matter content | 97.1 wt % |

Example 5

| Dextrose | 23.4 wt % |
|---|---|
| Acetylsalicylic acid | 75.0 wt % |
| Magnesium stearate | 0.5 wt % |
| Highly disperse $SiO_2$ | 0.1 wt % |
| Colourings and Flavourings | 1.0 wt % |
| Shape | cylindrical, flat |
| Weight | 0.68 g |
| Dry matter content | 98.9 wt % |

Example 6

| Dry glucose syrup | 23.4 wt % |
|---|---|
| Powder mix probiotic bacteria cultures with at least $1 \cdot 10^9$ CFU/g | 75.0 wt % |
| Magnesium stearate | 0.5 wt % |
| Highly disperse $SiO_2$ | 0.1 wt % |
| Colouring | 1.0 wt % |
| Shape | cylindrical, flat |
| Weight | 0.88 g |
| Dry matter content | 92.1 wt % |

Parameters of the Production Method and of the Produced Gelatin Products

Relevant parameters of the casting compound, of the core component, of the production method, and of the produced gelatin products (end product) are specified in the following table.

|  | Example 1 | Example 2 | Example 3 |
|---|---|---|---|
| Dry matter content of the casting compound before casting | 77.5 wt % | 78.7 wt % | 79.0 wt % |
| Quantity of casting compound | 4.0 g | 3.385 g | 3.0 g |
| Temperature of the casting head (casting temperature) | 83° C. | 83° C. | 82° C. |
| Dry matter content of the core component | 98.2 wt % | 99.9 wt % | 99.9 wt % |
| Quantity of core component | 1.0 g | 0.615 | 0.5 g |
| Total mass of the end product | 5.0 g | 4.000 g | 3.5 g |
| Proportion of the core component in the total mass | 20% | 15.4% | 14.3% |
| Dry matter content of the end product after the water balancing between core/gelatin gel | 81.8 wt % | 82.0 wt % | 82.0 wt % |
| $a_w$ value (25° C.) of the end product after the water balancing between core/gelatin gel | 0.692 | 0.663 | 0.694 |

|  | Example 4 | Example 5 | Example 6 |
|---|---|---|---|
| Dry matter content of the casting compound before casting | 77.5 wt % | 76.7 wt % | 74.5 wt % |
| Quantity of casting compound | 3.2 g | 2.32 g | 2.12 g |
| Temperature of the casting head (casting temperature) | 83° C. | 78° C. | 72° C. |
| Dry matter content of the core component | 97.1 wt % | 98.9 wt % | 92.1 wt % |
| Quantity of core component | 0.8 g | 0.68 g | 0.88 g |
| Total mass of the end product | 4.0 g | 3.00 g | 3.0 g |
| Proportion of the core component in the total mass | 20% | 22.7% | 29.3% |
| Dry matter content of the end product after the water balancing between core/gelatin gel | 82.0 wt % | 82.0 wt % | 82.0 wt % |
| $a_w$ value (25° C.) of the end product after the water balancing between core/gelatin gel | 0.651 | 0.674 | 0.649 |

The invention claimed is:

1. A gelatin product comprising a core component, wherein the core component is encased partially or fully by a gelatin gel, wherein the gelatin gel is produced from a homogeneous casting compound containing the following constituents dissolved in water:
   3 to 20 wt % of gelatin having a mean molecular weight, determined by gel chromatography, of at least 130 kDa, wherein the proportion of the molecular weight fraction above 100 kDa is at least 35 wt %;
   15 to 60 wt % of glucose syrup with a viscosity of less than 1000 mPa·s, measured with a dry matter content of 80 wt % and at a temperature of 60° C., wherein the glucose syrup has a dextrose equivalent of 50 or more; and
   15 to 60 wt % of sucrose,
   wherein the casting compound comprises a dry matter content of at least 70 wt %, and
   wherein the gelatin is obtained from connective tissue or bones of pigs, cattle or poultry.

2. The gelatin product according to claim 1, wherein the casting compound also contains one or more flavorings, colorings, and/or acidifiers.

3. The gelatin product according to claim 1, wherein the gelatin is contained in the casting compound in a proportion of from 5 to 12 wt %.

4. The gelatin product according to claim 1, wherein the glucose syrup and/or the sucrose are/is contained in the casting compound in each case in a proportion of from 20 to 40 wt %.

5. The gelatin product according to claim 1, wherein the casting compound also contains one or more sugar substitutes in a proportion of up to 80 wt %.

6. The gelatin product according to claim 5, wherein the one or more sugar substitutes is/are selected from polydextrose, hydrogenated glucose syrup and resistant dextrin, and/or wherein the one or more sugar alcohols is/are selected from sorbitol, mannitol, xylitol, erythritol and glycerol.

7. The gelatin product according to claim 1, wherein the casting compound also contains one or more further hydrocolloids in a proportion of from 0.1 to 10 wt %.

8. The gelatin product according to claim 1, wherein the core component is a shaped body which is produced from a solid-substance mixture.

9. The gelatin product according to claim 8, wherein the shaped body has a characteristic shape, surface structure and/or color, so as to enable the gelatin product to be visually recognizable, and wherein the shaped body deviates significantly in particular from a simple geometric shape, such as a sphere, an ellipsoid, or a cylinder.

10. The gelatin product according to claim 1, wherein the core component comprises one or more sugars, sugar substitutes and/or polysaccharides as basic constituents.

11. The gelatin product according to claim 10, wherein the one or more basic constituents of the core component is/are selected from glucose, fructose, lactose, sucrose, sorbitol, mannitol, xylitol, erythritol, starch, modified starch, cellulose, modified cellulose and mixtures thereof.

12. The gelatin product according to claim 1, wherein the core component also comprises one or more pharmaceutical active substances and/or nutrients.

13. The gelatin product according to claim 1, wherein the core component has hygroscopic properties.

14. The gelatin product according to claim 1, wherein the gelatin product has a dry matter content of more than 80 wt % and/or a water activity ($a_w$ value) of less than 0.75.

15. The gelatin product according to claim 1, wherein the core component accounts for a proportion of from 2 to 60% of the total mass of the gelatin product.

16. The gelatin product according to claim 1, wherein the total mass of the gelatin product lies in the range of from 1 to 10 g.

17. A method for producing a gelatin product comprising a core component according to claim 1, comprising:
   pouring a first amount of the casting compound at a temperature of 75° C. or more into a hollow mold;
   cooling the casting compound as appropriate;
   placing the core component in the hollow mold;

pouring a second amount of the casting compound at a temperature of 75° C. or more into the hollow mold;

cooling the casting compound in the hollow mold to a temperature of 25° C. or below in order to obtain the gelatin product; and removing the gelatin product from the hollow mold as appropriate.

18. The method according to claim 17, wherein the hollow mold is a solid hollow mold, which is made of a plastics material.

19. The method according to claim 17, wherein the casting compound is cooled in the hollow mold within a period of less than 60 min.

20. The method according to claim 17, wherein the casting compound is cooled in the hollow mold by means of an active cooling of the hollow mold.

* * * * *